(12) United States Patent
Hwang et al.

(10) Patent No.: US 10,937,546 B2
(45) Date of Patent: Mar. 2, 2021

(54) DEGREE-OF-DISTRACTION ESTIMATION SYSTEM BASED ON UNCONSTRAINED BIO-INFORMATION

(71) Applicant: DONGSEO TECHNOLOGY HEADQUTERS, Busan (KR)

(72) Inventors: Woo Jin Hwang, Busan (KR); Do Un Jeong, Busan (KR); Gi Hyun Hwang, Busan (KR); Dae-Soo Cho, Busan (KR)

(73) Assignee: Dongseo University Industry-Academic Cooperation Foundation, Busan (KR)

( * ) Notice: Subject to any disclaimer, the term of this patent is extended or adjusted under 35 U.S.C. 154(b) by 0 days.

(21) Appl. No.: 15/502,945

(22) PCT Filed: Feb. 18, 2016

(86) PCT No.: PCT/KR2016/001657
§ 371 (c)(1),
(2) Date: Feb. 9, 2017

(87) PCT Pub. No.: WO2017/135492
PCT Pub. Date: Aug. 10, 2017

(65) Prior Publication Data
US 2018/0336968 A1    Nov. 22, 2018

(30) Foreign Application Priority Data

Feb. 3, 2016    (KR) ........................ 10-2016-0013625

(51) Int. Cl.
*G16H 50/20*    (2018.01)
*A61B 5/16*    (2006.01)
(Continued)

(52) U.S. Cl.
CPC ........... *G16H 50/20* (2018.01); *A61B 5/1036* (2013.01); *A61B 5/11* (2013.01); *A61B 5/16* (2013.01);
(Continued)

(58) Field of Classification Search
CPC .................................................... G16H 50/20
See application file for complete search history.

(56) References Cited

U.S. PATENT DOCUMENTS

2003/0233034 A1    12/2003   Varri et al.
2007/0192038 A1*   8/2007   Kameyama ............. G06F 16/48
                                                                    702/19
(Continued)

FOREIGN PATENT DOCUMENTS

JP    2003-111646 A    4/2003
KR    10-0697211 B1    3/2007
(Continued)

*Primary Examiner* — Lynsey C Eiseman
*Assistant Examiner* — Amanda L Steinberg (57) ABSTRACT

The present invention relates to a system for estimating a degree of distraction based on unconstrained bio-information. The present invention provides a system for estimating a degree of distraction based on unconstrained bio-information, the system comprising: a degree-of-distraction measurement chair comprising a seating unit, a message transmission unit, a pressure detection unit, and a support unit, which are formed in this order from the top to the bottom thereof, wherein the pressure detection unit formed on the support unit comprises a smart sensor including three load cells arranged at three vertices of a triangular shape on a plane; and a mobile smart terminal configured to receive information regarding the degree of distraction from the message transmission unit of the degree-of-distraction measurement chair through the Bluetooth communication.

20 Claims, 7 Drawing Sheets (51) Int. Cl.
    *A61B 5/11*          (2006.01)
    *A61B 5/103*        (2006.01)
    *A61B 5/00*          (2006.01)
    *G16H 50/30*       (2018.01)
    *G16H 40/63*       (2018.01)
    *G16H 15/00*       (2018.01)
    *A61B 5/0476*      (2006.01)

(52) U.S. Cl.
    CPC ........... *A61B 5/6891* (2013.01); *G16H 15/00* (2018.01); *G16H 40/63* (2018.01); *G16H 50/30* (2018.01); *A61B 5/0476* (2013.01)

(56) References Cited

U.S. PATENT DOCUMENTS

| | | | | |
|---|---|---|---|---|
| 2012/0271122 A1* | 10/2012 | David | .................. | A61B 5/0205 |
| | | | | 600/301 |
| 2016/0090097 A1* | 3/2016 | Grube | ...................... | A61B 5/18 |
| | | | | 340/576 |
| 2016/0354027 A1* | 12/2016 | Benson | ................ | A61M 21/02 |
| 2017/0067774 A1* | 3/2017 | Gough | ................. | G01G 3/1402 |

FOREIGN PATENT DOCUMENTS

| | | |
|---|---|---|
| KR | 10-2009-0104358 A | 10/2009 |
| KR | 10-2015-0094316 A | 8/2015 |

\* cited by examiner

DEGREE-OF-DISTRACTION ESTIMATION SYSTEM BASED ON UNCONSTRAINED BIO-INFORMATION

TECHNICAL FIELD

The present invention relates to a system for estimating a degree of distraction based on unconstrained bio-information, and more particularly, to such a system for estimating a degree of distraction based on unconstrained bio-information, in which when a subject is seated on a chair, a monitoring operation is performed to estimate the degree of distraction from seating information.

BACKGROUND ART

A healthcare technology provides various disease control solutions through a disease treatment process as well as a disease pre-monitoring and prevention process. Such a healthcare technology is recently extended from a hospital-centered healthcare area to a daily life area.

In particular, various studies are attempted on bio-signal measurement-based real-time healthcare using a sensor attached to a subject's body and unconstrained unconscious health monitoring. In recent years, as Internet of Things (hereinafter, referred to as "IoT") technology comes into focus, the results of the studies are applied to the health monitoring field in our daily life.

A ballistocardiogram measurement and analysis related technique is proposed in an existing degree-of-distraction estimation method. In this case, a technique has been proposed in which an electromechanical film (EMFi) is attached to a chair to measure the ballistocardiogram. However, in the case of a cushion type sensor using the EMFi sensor, an energy dispersion phenomenon occurs and it is difficult to acquire a high quality signal due to introduction of a motion artifact caused by motion. In addition, the magnitude and frequency of the motion can be measured, but utility of the cushion type sensor is disadvantageously restricted due to loss of directional information (vector). Besides, the cushion type sensor also has a limitation in that a motion (i.e., a degree of distraction) can be estimated but posture information is impossible to analyze.

Moreover, the most useful tool in the existing degree-of-distraction estimation method is a brain-waves measuring instrument. A disorder of attention and concentration can be determined by measuring a variation in brain waves in a simple situation. In addition, the accuracy of the measurement is approximately 95%, which is a level that enables the clinical use.

DISCLOSURE OF INVENTION

Technical Problem

Accordingly, the present invention has been made in order to solve the above-described problems occurring in the prior art, and it is an object of the present invention to a system for estimating a degree of distraction based on unconstrained bio-information, in which a change rate of the posture is monitored in a daily life and a degree of distraction reflecting the amount of motion generated during the seating time is provided.

Another object of the present invention is to provide a system for estimating a degree of distraction based on unconstrained bio-information, which is configured to be utilized as a healthcare parameter that can be determined by measuring the unstable state of a sitter due to a peripheral stimulus or a variation of the posture using the degree of distraction.

Still another object of the present invention is to provide a system for estimating a degree of distraction based on unconstrained bio-information, which is closely related to efficiency of learning and is reflected to a degree of learning performance by raising a problem of a sitter's attention and degree of distraction that are repeated continuously.

However, objects which are to be achieved by the present invention are not limited to the above-mentioned objects, and other objects of the present invention will be clearly understood by those skilled in the art from the following description.

Technical Solution

To achieve the above objects, the present invention provides a system for estimating a degree of distraction based on unconstrained bio-information, the system comprising: a degree-of-distraction measurement chair comprising a seating unit, a message transmission unit, a pressure detection unit, and a support unit, which are formed in this order from the top to the bottom thereof, wherein the pressure detection unit formed on the support unit comprises a smart sensor including three load cells arranged at three vertices of a triangular shape on a plane; and a mobile smart terminal configured to receive information regarding the degree of distraction from the message transmission unit of the degree-of-distraction measurement chair through the Bluetooth communication. The smart sensor is formed as a multi-channel sensor for simultaneously monitoring multiple items of information (e.g., posture information, ballistocardiogram, and body weight) using the three load cells that are multi-sensor-based posture measuring sensors and simultaneously measuring the magnitude and directional value of the posture information. The message transmission unit comprises an interface module comprising a microprocessor configured to be connectable to an external sensor through an extension connector to allow for bio-measurement and configured to perform A/D conversion of an acquired bio-measurement signal and wireless transmission of data. The microprocessor extracts, from the smart sensor, a sitter's body weight information measured one time when the sitter is first seated on the degree-of-distraction measurement chair upon the monitoring of posture information, and detects a change in posture distribution from the distribution of the body weight information received by the smart sensor through creation of correction information of preset correct posture information.

Advantageous Effects

The system for estimating a degree of distraction based on unconstrained bio-information according to an embodiment of the present invention has the effects that a change rate of the posture can be monitored in a daily life and a degree of distraction reflecting the amount of motion generated during the seating time can be provided.

In addition, the system for estimating a degree of distraction based on unconstrained bio-information according to an embodiment of the present invention provides an effect that it can be utilized as a healthcare parameter that can be determined by measuring the unstable state of a sitter due to a peripheral stimulus or a variation of the posture using the degree of distraction.

Further, the system for estimating a degree of distraction based on unconstrained bio-information according to an embodiment of the present invention has an effect that it is closely related to efficiency of learning and can be reflected to a degree of learning performance by raising a problem of a sitter's attention and degree of distraction that are repeated continuously.

BRIEF DESCRIPTION OF THE DRAWINGS

The above and other objects, features and advantages of the present invention will be apparent from the following detailed description of the preferred embodiments of the invention in conjunction with the accompanying drawings, in which.

BEST MODE FOR CARRYING OUT THE INVENTION

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

In the specification, when any one component 'transmits' data or a signal to another component, it may directly transmit the data or signal to the other component or transmit the data or signal to the other component through at least one other component.

Figure 1:
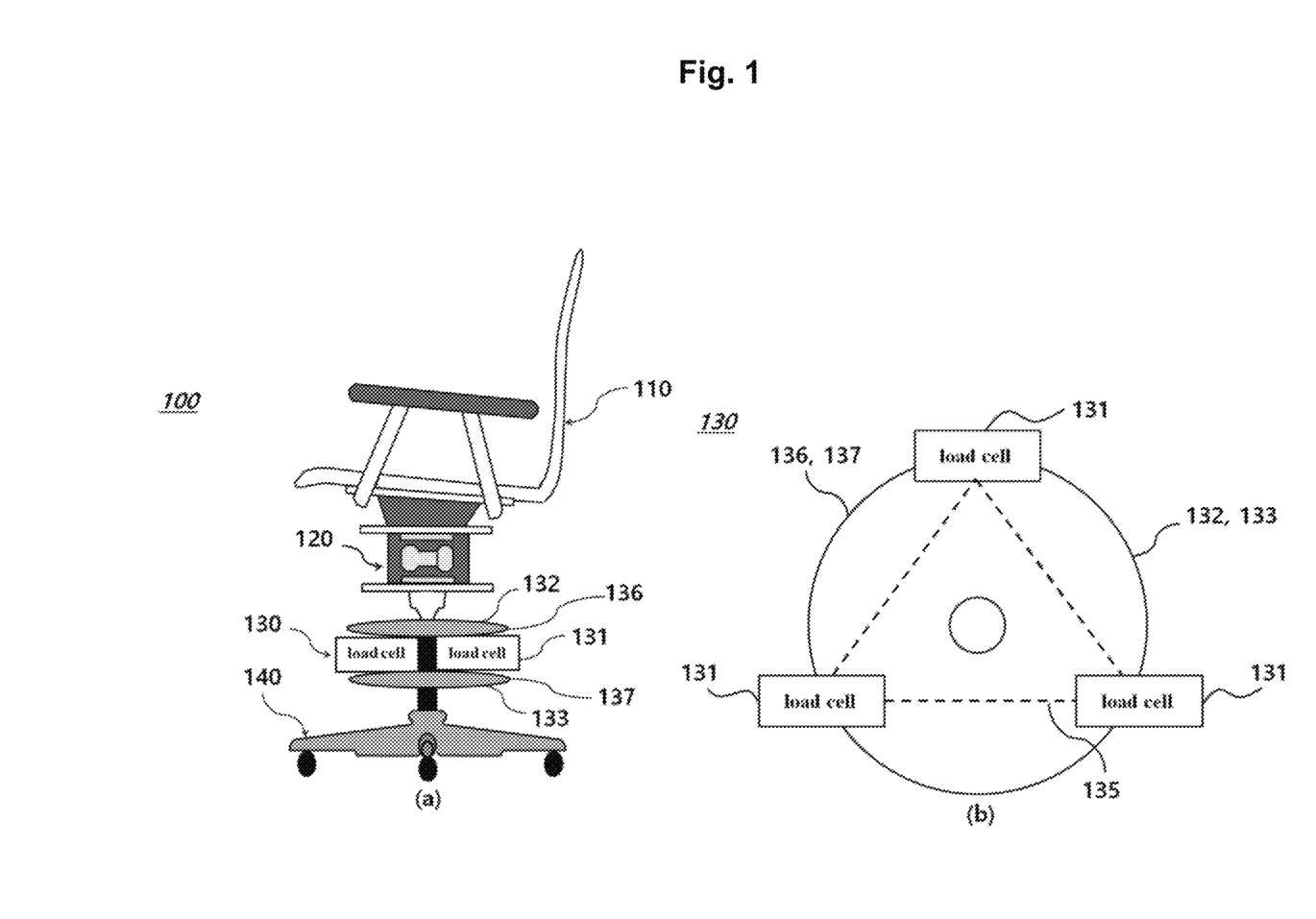
FIG. 1 is a schematic view showing a degree-of-distraction measurement chair in a degree-of-distraction estimation system based on unconstrained bio-information according to an embodiment of the present invention.

FIG. 1 is a schematic view showing a degree-of-distraction measurement chair in a degree-of-distraction estimation system based on unconstrained bio-information according to an embodiment of the present invention. Referring to FIG. 1, the degree-of-distraction measurement chair 100 includes a seating unit 110, a message transmission unit 120, a pressure detection unit 130, and a support unit 140.

In this case, the seating unit 110, the message transmission unit 120, the pressure detection unit 130, and the support unit 140 are formed in this order from the top to the bottom of the degree-of-distraction measurement chair 100. The pressure detection unit 130 formed on the support unit 140 includes three load cells 131 arranged at three vertices of a triangular shape 135 on a plane. The pressure detection unit 130 further comprises of a upper disk 132 having a upper disk outer edge 136 and a lower disk 133 having lower disk outer edge 137 so that the three load cells 131 are placed in between the upper disk 132 and the lower disk 133 and each of the three load cells 131 are placed near the upper disk outer edge 136 and the lower disk outer edge 137.

Figure 2:
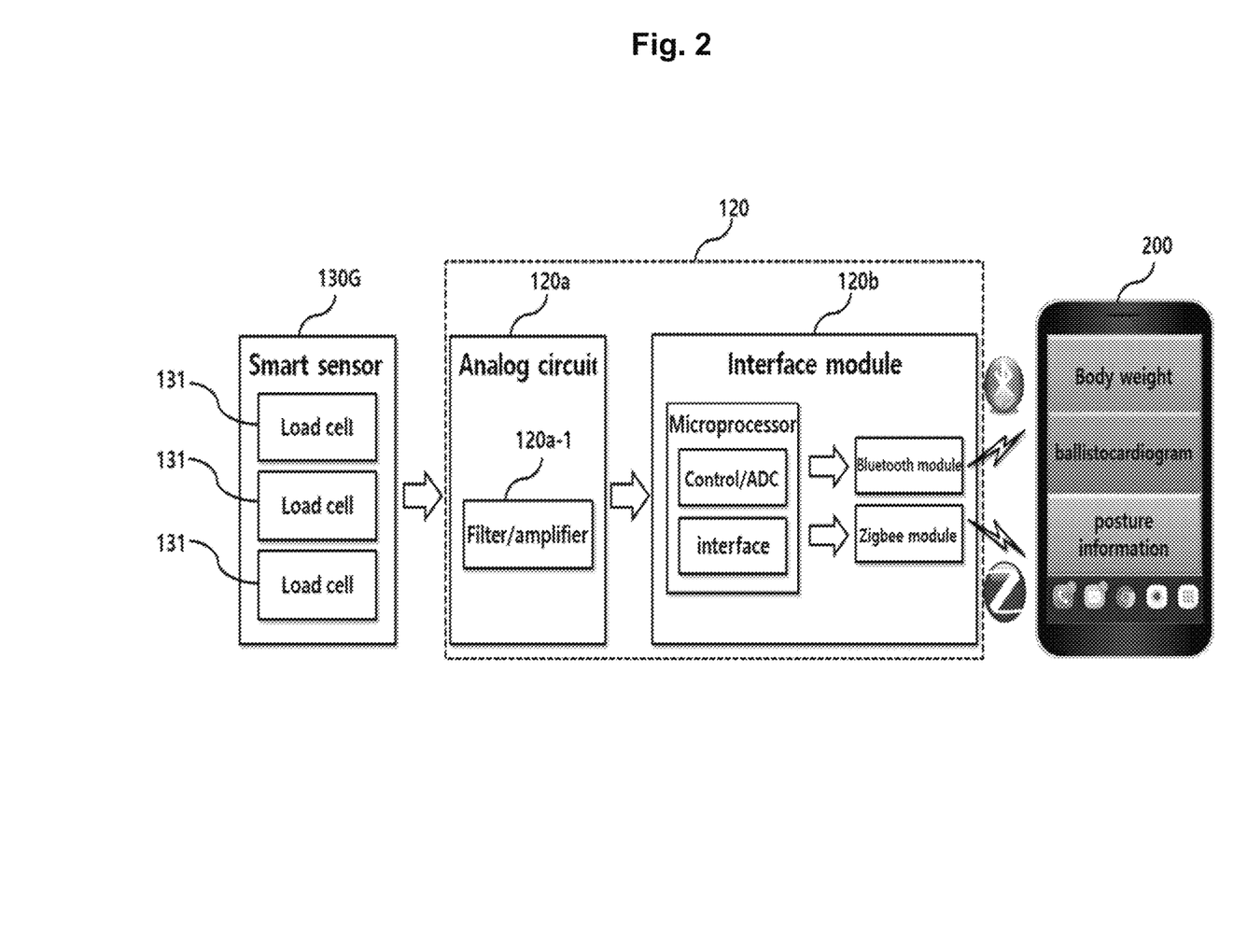
FIG. 2 is a block diagram showing a degree-of-distraction estimation system based on unconstrained bio-information according to an embodiment of the present invention.

FIG. 2 is a block diagram showing a degree-of-distraction estimation system based on unconstrained bio-information according to an embodiment of the present invention. Referring to FIG. 2, the degree-of-distraction estimation system based on unconstrained bio-information may include a smart sensor 130G consisting of three load cells 131 formed at the pressure detection unit 130, an analog circuit 120a and an interface module 120b that constitute the message transmission unit 120, and a mobile smart terminal 200.

The smart sensor 130G is a multi-sensor-based posture measuring sensor, which acts to monitor multiple items of information (e.g., posture information, ballistocardiogram, and body weight) at the same time, and is formed as a multi-channel sensor for simultaneously measuring the magnitude and directional value of the posture information.

In other words, the three-vertex load cells 131 included in the smart sensor 130G detect, as an electric signal, the amount of deformation according to a load, and the load cells 131 are preferably provided in three numbers between an upper plate and a lower plate constituting the pressure detection unit 130 of the degree-of-distraction measurement chair 100. The smart sensor 130G can improve the signal-to-noise (S/N) ratio of a signal because the body weight and ballistocardiogram are concentrated on the three load cells 131.

In another embodiment of the present invention, the smart sensor 130G may be provided as a modified ferroelectric sensor. In this case, a permanently charged ferroelectric film that converts mechanical pressure into electrical energy is attached onto the upper plate and the lower plate of the pressure detection unit 130 of the degree-of-distraction measurement chair 100. The permanently charged ferroelectric film can provide an advantage in that it can be manufactured in a mat shape to facilitate the measurement experiment.

In addition, in still another embodiment of the present invention, the smart sensor 130G may be implemented as a piezoelectric sensor array using a piezoelectric or pressure sensor, or may be implemented as an air cushion-embedded pressure sensor to detect the change.

Hereinafter, the addition and use of the ferroelectric sensor will be described centering on the three-vertex load cells 131 constituting the smart sensor 130G.

In the present invention, because ballistocardiogram and concurrent measurement must be taken into consideration, the degree-of-distraction estimation system includes an analog circuit 120a constituting the message transmission unit 120 as a separate circuit configuration for removing the motion artifact characteristics according to a motion of a sitter so that the motion artifact can be removed by a filter/amplifier 120a-1 of the analog circuit 120a.

In this case, the filter/amplifier 120a-1 is configured to include a high-pass filter for removing an offset caused by the body weight, an amplifier for amplifying a fine signal, and a low-pass filter for removing a noise to thereby detect a final ballistocardiogram signal.

Referring to FIG. 2, the degree-of-distraction estimation system based on unconstrained bio-information according to the present invention can construct a wireless transmission system for transmitting data to the mobile smart terminal 200 such as a wired terminal (not shown) like a PC, a smartphone, or a smart pad through a near filed communication scheme by a Bluetooth module and a Zigbee module of the interface module 120b after A/D conversion of body weight, posture information, ballistocardiogram information that are measured by the smart sensor 130G composed of multi-load cells.

To this end, a wireless sensor network technology based on IEEE 802.15.4 or a general-purpose Bluetooth communication technique is applied to the degree-of-distraction estimation system of the present invention. In the case where the wireless sensor network technology is applied to the degree-of-distraction estimation system, the degree-of-distraction estimation system must be provided with a separate dongle system for interfacing at the mobile smart terminal 200 and has an advantage in that an ultra-low power interface is possible.

The interface module 120b constituting the message transmission unit 120 is composed of an MSP430F1611 (TI, USA) microcontroller employing a low-priced, high-capacity flash memory, a RF transceiver (CC2420, Chipcon AS, Norway) employing IEEE 802.15.4, and an external flash memory (M25P80, STMicroelectronics, USA) so that the interface module 120b can be extended with a surrounding interface, and thus can allow the degree-of-distraction measurement chair 100 to constitute the degree-of-distraction estimation system based on unconstrained bio-information with a wireless sensor node.

A sensor node configured by the interface module 120b has an advantage in that it is connectable to an external sensor through an extension connector to allow for bio-measurement, and can support TinyOS to maintain compatibility with an existing wireless sensor network.

Meanwhile, in the case where a Bluetooth communication scheme is applied to configure the degree-of-distraction estimation system based on unconstrained bio-information using the interface module 120b, the mobile smart terminal 200 does not need a separate dongle system but the degree-of-distraction measurement chair 100 requires a configuration of a system for applying the Bluetooth wireless communication. In addition, the present invention provides the interface module 120b based on the microprocessor to perform A/D conversion of a signal acquired through the smart sensor 130G of the degree-of-distraction measurement chair 100 and wireless transmission of data.

The microprocessor of the interface module 120b is implemented using an ATmega8L processor (manufactured by Atmel) that can exhibit a low power high performance in order to convert a ballistocardiogram analog signal to a digital signal and transmit the converted signal. The ATmega8L processor is an 8-bit RISC microcontroller that can operate even at a voltage of 3.3v, and is configured to enable the interfacing of various sensors for bio-measurement using analog and digital I/O ports.

In the meantime, the microprocessor of the interface module 120b performs the estimation of posture information.

To this end, the microprocessor of the interface module 120b extracts, from the smart sensor 130b, a sitter's body weight information measured one time when the sitter is first seated on the degree-of-distraction measurement chair upon the monitoring of posture information, and detects a change in posture distribution from the distribution of the body weight information received by the smart sensor 130G through creation of correction information of preset correct posture information.

The microprocessor of the interface module 120b can represent a posture change, i.e., the type of motion in the form of frequency and intensity, and estimates the posture information by separating frequency information of the posture change and intensity information of the posture change to comprehensively reflect the posture change on the evaluation of the degree of distraction.

In this case, the frequency information of the posture change means the number of generations per unit time of an inducing factor of the posture change according to motion, and the intensity information of the posture change means directionality as a magnitude of motion intended to be utilized as posture correction information through concurrent security.

Figure 3:
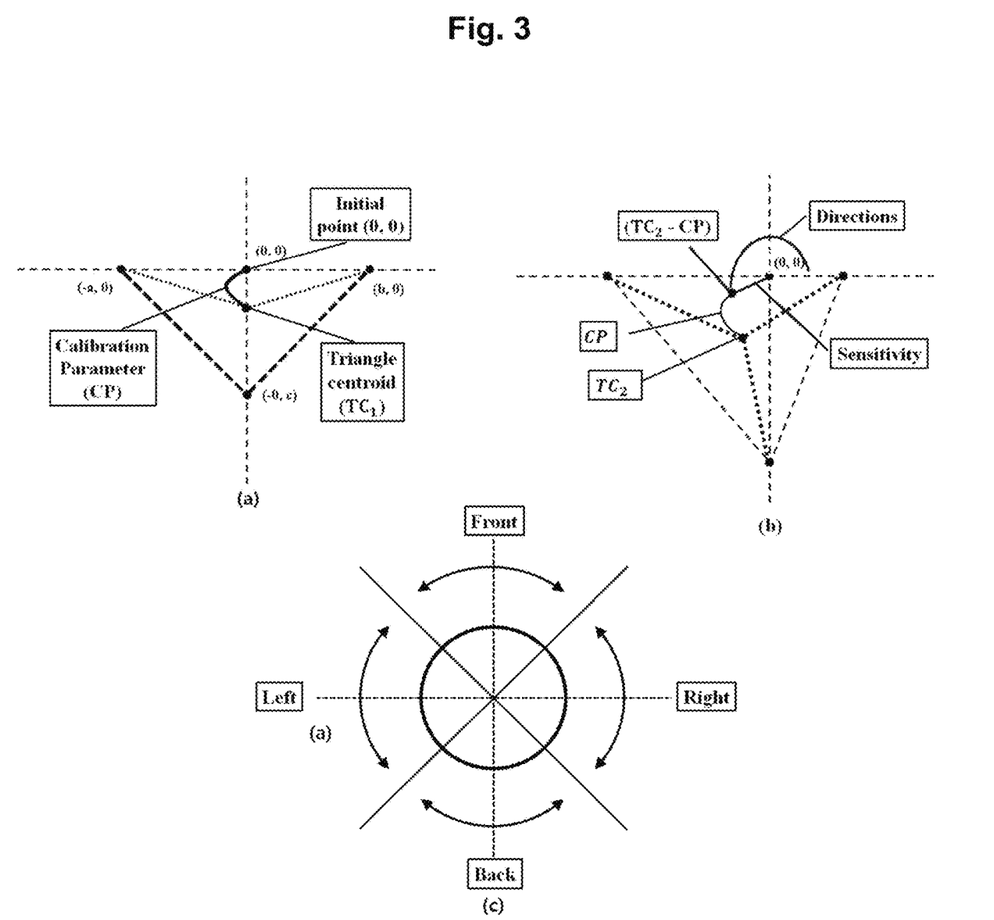
FIG. 3 is a diagram showing the generation of a posture variation parameter in a degree-of-distraction estimation system based on unconstrained bio-information according to an embodiment of the present invention.

FIG. 3a shows a three-point calibration of each load cell 131 by the microprocessor of the interface module 120b, FIG. 3b shows an estimation of sensitivity and directionality of posture information, and FIG. 3c shows generation of a parameter using directionality, magnitude, and frequency of a posture change.

Subsequently, a process of estimating a degree-of-distraction index based on a rate of posture change using the microprocessor of the interface module 120b will be described hereinafter.

The microprocessor of the interface module 120b can provide a posture change rate indicator and parameter using parameters (i.e., the frequency of the posture change and the intensity of the posture change) extracted from the posture change information.

The microprocessor of the interface module 120b extracts posture change information of a given time, targeted to a general subject (e.g., based on a healthy 20-year-old university student) and evaluates the frequency of the posture change (i.e., converts the frequency into a score distribution and utilizes it as a parameter).

In other words, the microprocessor of the interface module 120b calculates an average frequency through a measurement experiment and a statistical analysis, which are targeted to a plurality of subjects, and then makes a scoring list for the frequency based on a standard deviation using an intermediate value as an average value.

Accordingly, the microprocessor of the interface module 120b can generate a degree-of-distraction index through the analysis and comparison of brain waves. To this end, the interface module 120b is required to be operated in cooperation with an external brain wave measuring device.

Figure 4:
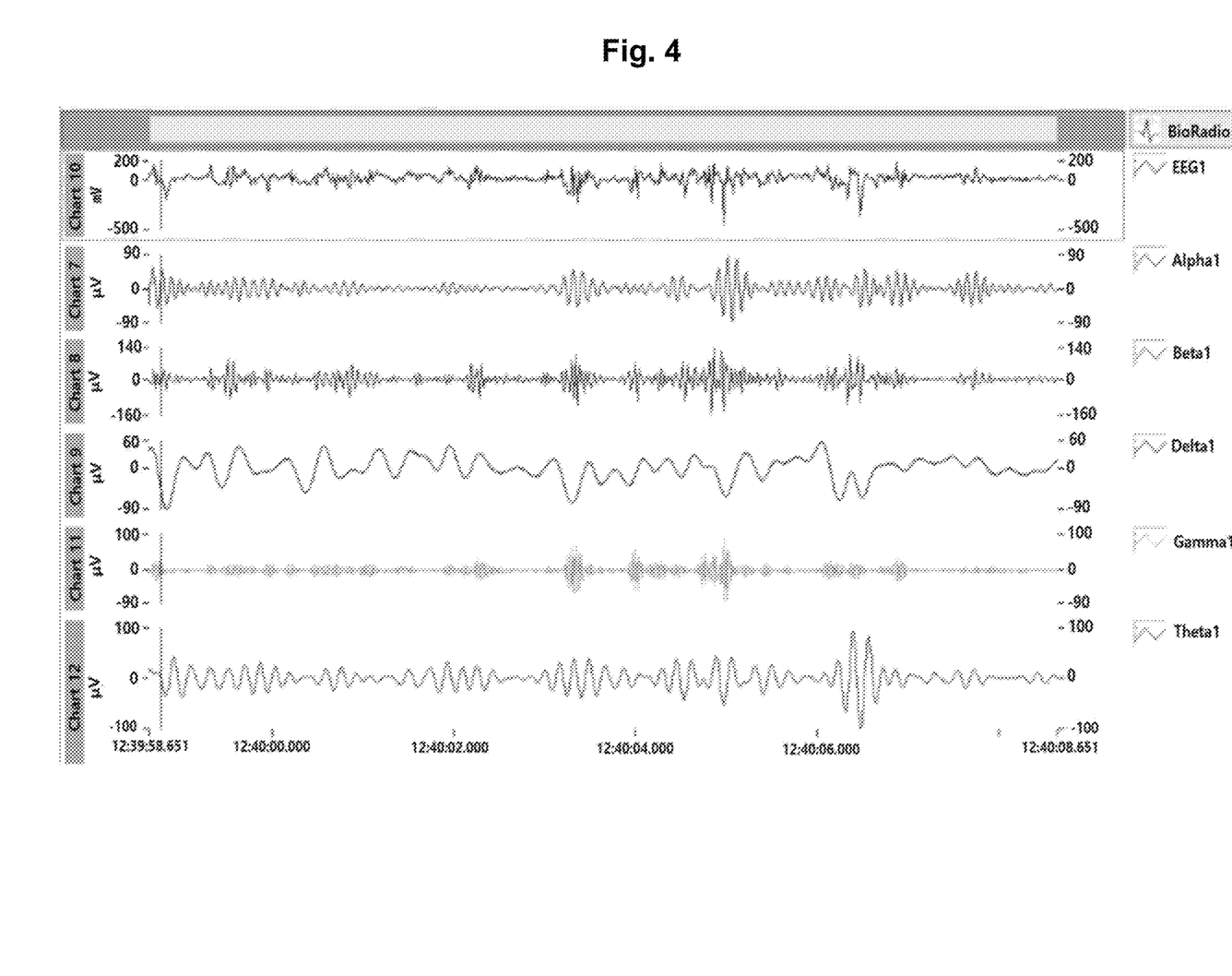
FIG. 4 is a diagram showing brain wave signals used in a degree-of-distraction estimation system based on unconstrained bio-information according to an embodiment of the present invention.

The relationship between degree of distraction (degree of concentration) and the characteristics of the brain wave will be described hereinafter. FIG. 4 is a reference graph showing brain wave signals extracted according to the analysis of a child's brain waves.

The brain wave is divided into an alpha ($\alpha$) wave, a beta ($\beta$) wave, a delta ($\delta$) wave and a theta ($\theta$) wave and has an electrical vibration and synchronization. For the electrical properties of a brain wave signal in a stable state in which a subject's eyes are closed, the brain wave signal mainly is within a voltage of 10-100 $\mu$V and a frequency of less than 100 Hz. Clinically useful information is almost included in a frequency of less than 35 Hz. The alpha wave is a typical waveform of the brain wave has a frequency of 8-13 Hz. The alpha wave has a property in which when a subject reaches a stable and concentrated state with him or her eyes closed, the alpha wave appears much at the occiput of the brain. In particular, the alpha wave appears the most strongly as a brain wave signal in a normal awareness state. In the case of a normal person, the alpha wave has an amplitude of 26-60 µN, and a signal greater than 60 µV is observed and is utilized much as a concentration indicator according to circumstances. The activity level of the alpha wave increases in proportion to age until a child becomes an adult. When the child becomes 21 years old, the alpha wave occupies approximately 70% of the entire activity level of the brain wave.

In the present invention, the microprocessor of the interface module 120b conducts comparison and evaluation through the alpha wave and the SMR wave of the brain wave, which is commonly utilized to perform a validity check of a degree-of-distraction parameter, minimizes a brainwave interference and an artifact generated from the subject's face in the concentrated and unconcentrated states, and monitors a brain wave signal.

The microprocessor of the interface module 120h performs an analysis of the correlation with an analysis of the brain wave. In the case of the brain wave, it is known to the academic world that the alpha wave (8-12 Hz) and the SMR wave (12-15 Hz) are related to concentration and are utilized much for analysis of concentration.

According to a report of the Academic Society that the alpha wave (8-12 Hz) and the SMR wave (12-15 Hz) is generated from the frontal lobe, the microprocessor of the interface module 120b performs a classification of a feature generated in a distracted state through a signal processing technique of minimizing an artifact signal generated from the subject's face and an interference brain wave generated from a site other than the frontal lobe.

Figure 5:
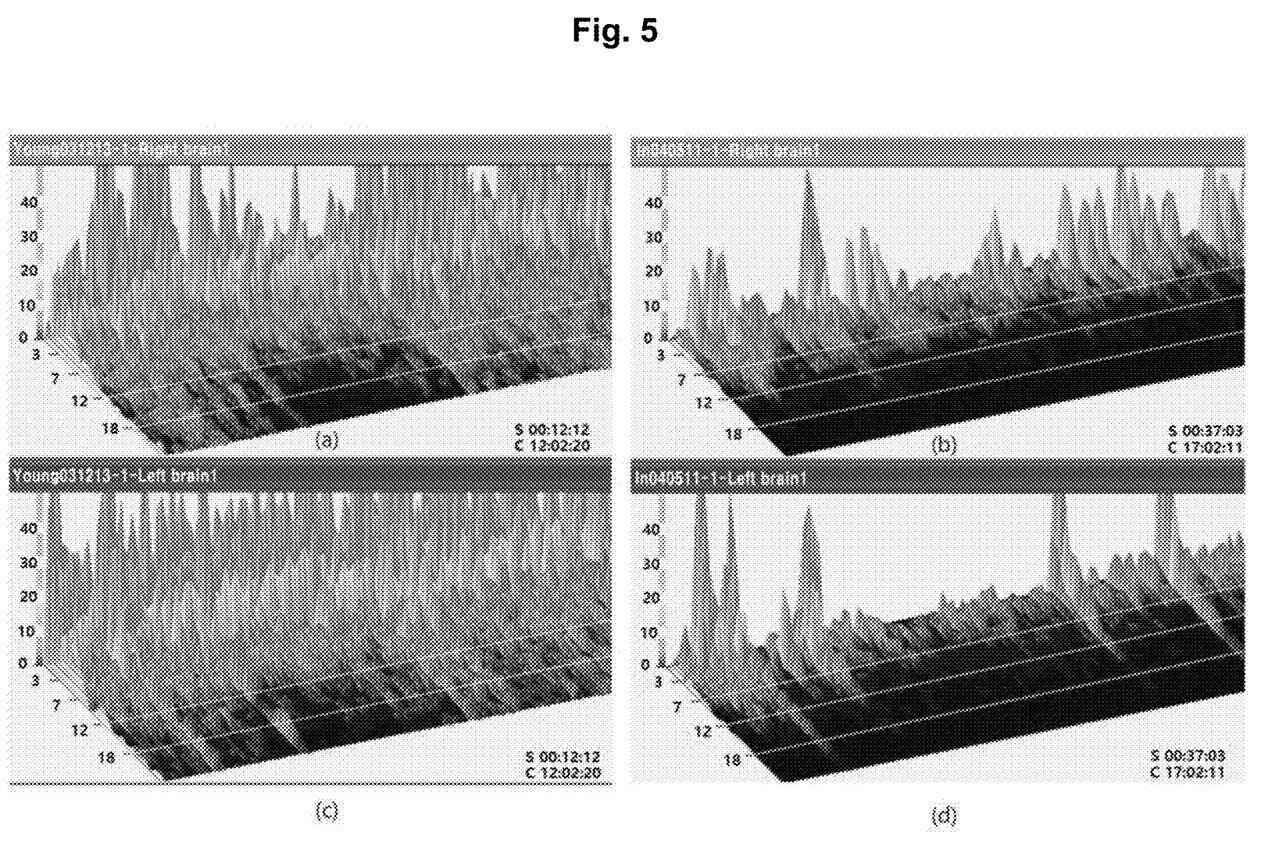
FIG. 5 is a graph showing a change in brain waves in accordance with concentration used in a degree-of-distraction estimation system based on unconstrained bio-information according to an embodiment of the present invention.

FIG. 5 is a graph showing examples of a change in brain waves in accordance with concentration, wherein FIG. 5a shows a brain wave measured in the left brain in a state where concentration is low, FIG. 5h shows a brain wave measured in the left brain in a state where concentration is high, FIG. 5c shows a brain wave measured in the right brain in a state where concentration is low, and FIG. 5b shows a brain wave measured in the right brain in a state where concentration is high.

The microprocessor of the interface module 120b estimates a degree of distraction based on the brain wave as an existing indicator that can be utilized for diagnosis clinically, and the system including a brain wave measuring device that is operated in cooperation with the interface module 120b performs the measurement centering on the frontal lobe using a commercialized brain wave measurement system to conduct a pre-processing process and a signal processing process.

In other words, the microprocessor of the interface module 120b analyzes the posture information in a seated state and the brain wave measured simultaneously with the posture information, and analyzes the correlation between a specific brain wave and a degree of distraction to create a degree-of-distraction parameter.

In this case, a degree of concentration that can be estimated through the brain wave is a concept opposite to a degree of distraction, and the microprocessor of the interface module 120b performs a correlation analysis on a power spectrum density (PSD) distribution characteristics or a specific waveform of the brain wave indicating the degree of distracting and the degree of concentration, and utilizes a result of the correlation analysis as a parameter.

Next, objectivity of a degree-of-distraction estimation parameter by the microprocessor of the interface module 120b will be described hereinafter. The microprocessor of the interface module 120b reflects how position information of the subject's body weight moves for a reference time in the case of a posture change, measures a moved distance and time, and uses the measured distance and time. In addition, the microprocessor of the interface module 120b monitors the frequency and intensity of motion, and then estimates the degree of distraction through quantification and parameterization.

In other words, the microprocessor of the interface module 120b can estimate even a symptom of the ADHD syndrome based on the tilt characteristics of a body weight distribution, as information that can be extracted from the posture information, and indirectly monitor whether or not the subject maintains a correct posture, aside from the estimation of the ADHD symptom.

In addition, the microprocessor of the interface module 120b can perform a correlation analysis with a parameter related to a degree of concentration extractable from the analysis of the brain wave. In this case, the microprocessor of the interface module 120b can use a frequency component ratio as an analysis parameter through an analysis of a specific waveform (a-wave) and PSD associated with a degree of concentration of the brain wave and a change in degree-of-distraction index per unit time, and perform an indirect monitoring of the degree of concentration although a cumbersome brain wave measurement and analysis is not performed if significance is secured through the correlation analysis with the degree of concentration.

Further, the microprocessor of the interface module 120b can perform a correlation analysis on the degree of distraction and a behavior pattern through video analysis. In this case, the microprocessor of the interface module 120b can perform a posture change analysis, a brain wave analysis, and a video analysis using a web camera simultaneously, and analyze the correlation between parameters for the posture change analysis and the brain wave analysis using a result of the video analysis as a reference data so that big data can be secured through a long-term data analysis.

Subsequently, a field test for simultaneously monitoring a change rate of the posture and a correct posture, which was conducted by the microprocessor of the interface module 120b will be described hereinafter.

A posture change in a seated state reflects the movement or fluctuation of a sitter's gaze by an external stimulus. Thus, the microprocessor of the interface module 120b can identify the sitter's habit and check a change rate of the posture per unit time by measuring a continuous change state.

Accordingly, the present invention has evaluated a possibility of detection of a signal at each posture and proposed the pre-study data to concurrently proceed the estimation experiments of the posture change and the degree of distraction based on the pre-study, so that the system of the present invention can suggest a degree-of-distraction estimation parameter robust against various external environments by observing a degree of change of the degree-of-distraction estimation parameter according to the posture to reflect the degree of change on the analysis.

Figure 6:
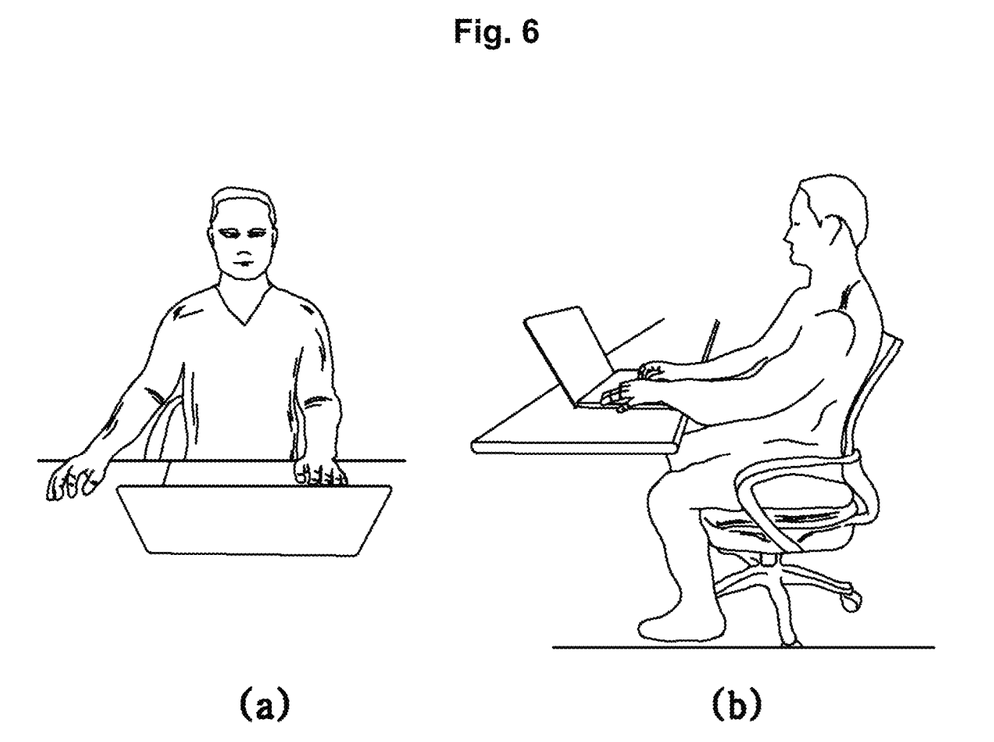
FIGS. 6 and 7 are diagrams showing a state in which a subject is determined to take a normal posture and a state in which the subject is determined to take an abnormal posture in a degree-of-distraction estimation system based on unconstrained bio-information according to an embodiment of the present invention.
Figure 7:
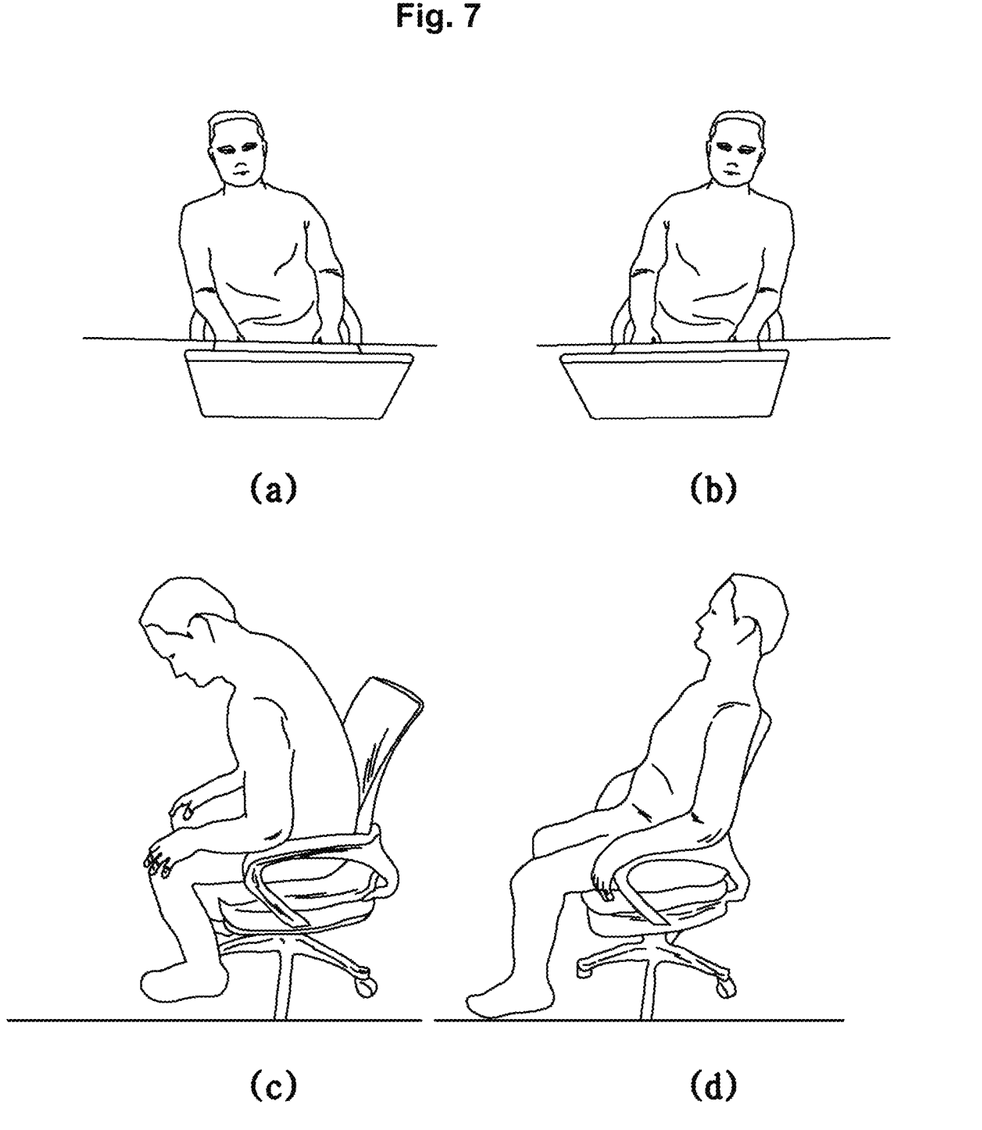

FIG. 6 shows a state in which a subject is determined to take a normal posture based on the degree-of-distraction estimation parameter and FIG. 7 shows a state in which the subject is determined to take an abnormal posture based on the degree-of-distraction estimation parameter.

The posture information at the time of estimation of the degree of distraction according to the present invention and the additionally detectable Ballistocardiogram information can be usefully utilized in health monitoring applications such as posture correction and unconstrained heart rate monitoring in a daily life In addition, the present invention can be utilized in real-time health monitoring applications by performing an analysis of the heart beat based on the detection of the implemented unconstrained ballistocardiogram feature (J-peak), and enables to discover the subject of a follow-up study, such as the correlation between the degree of distraction and HRV. The unconstrained ballistocardiogram feature (J-peak) is similar to electrocardiogram (ECG), and thus has a significance and can be utilized as a key indicator of determining an abnormal sign of heart activity.

As described above, while preferred embodiments of the present invention have been disclosed in this specification and the drawings and specific terms have been used, these terms are used in a general means to easily describe the technical spirit of the present invention and help to understand the invention, but is not intended to limit the scope of the present invention. It will be obvious to a person of ordinary skill in the art that other modifications based on the technical spirit of the present invention besides embodiments set forth herein can be carried out.

BEST MODE

The degree-of-distraction measurement chair 100 of a degree-of-distraction estimation system based on unconstrained bio-information according to an embodiment of the present invention includes a seating unit 110, a message transmission unit 120, a pressure detection unit 130, and a support unit 140.

The degree-of-distraction estimation system based on unconstrained bio-information according to an embodiment of the present invention is configured to include a smart sensor 130G consisting of three load cells 131 formed at the pressure detection unit 130, an analog circuit 120a and an interface module 120b that constitute the message transmission unit 120, and a mobile smart terminal 200.

In the case where a Bluetooth communication scheme is applied to configure the degree-of-distraction estimation system based on unconstrained bio-information using the interface module 120b, the mobile smart terminal 200 does not need a separate dongle system but the degree-of-distraction measurement chair 100 requires a configuration of a system for applying the Bluetooth wireless communication. In addition, the present invention provides the interface module 120b based on the microprocessor to perform A/D conversion of a signal acquired through the smart sensor 130G of the degree-of-distraction measurement chair (100 and wireless transmission of data.

In this case, preferably, the microprocessor monitors a posture change (i.e., the type of motion) in the form of frequency and intensity, estimates the posture information by separating frequency information of the posture change and intensity information of the posture change, and reflects the posture information on the evaluation of degree of distraction.

In addition, preferably, the frequency information of the posture change is the number of generations per unit time of an inducing factor of the posture change according to motion, and the intensity information of the posture change is directionality as a magnitude of motion.

Further, preferably, the microprocessor provides a posture change rate indicator and parameter using parameters (i.e., the frequency of the posture change and the intensity of the posture change) extracted upon the monitoring of the posture change, at which time, the microprocessor calculates an average frequency through a measurement experiment and a statistical analysis, which are targeted to a plurality of subjects, and then provides the frequency by scoring the frequency based on a standard deviation using an intermediate value as an average value.

Besides, preferably, the microprocessor receives a brain wave signal from an external brain wave measuring device connected to the interface module in order to generate a degree-of-distraction index through the analysis and comparison of brain waves, conducts comparison and evaluation based on preset reference brain wave information (i.e., brain wave information measured in the left brain in a state where concentration is low (a description of FIG. 5a), brain wave information measured in the left brain in a state where concentration is high (a description of FIG. 5h), brain wave information measured in the right brain in a state where concentration is low (a description of FIG. 5c), and brain wave information measured in the right brain in a state where concentration is high (a description of FIG. 5d)) and an alpha ($\alpha$) wave and an SMR wave of a brain wave extracted by the brain wave measuring device, analyzes the posture information in a seated state and the brain wave measured simultaneously with the posture information upon the monitoring of the brain wave signal at a concentrated state and an unconcentrated state, and analyzes the correlation between the extracted brain wave and the degree of distraction to thereby generate a degree-of-distraction parameter.

INDUSTRIAL APPLICABILITY

The degree-of-distraction estimation system based on unconstrained bio-information according to an embodiment of the present invention allows a considerable number of ADHD symptoms to appear as the form of motion, which includes a factor enabling the monitoring in state in which a subject is seated on the chair, and thus the degree-of-distraction estimation system can be utilized in the monitoring applications of a degree of concentration and the ADHD symptoms through the degree-of-distraction index.

The invention claimed is:

1. A system for estimating a degree of distraction of a user based on unconstrained bio-information obtained from the user, comprising:
   a chair comprising a seating unit, a pressure detection unit and a support unit, the pressure detection located between the seating unit and the support unit,
   wherein the pressure detection unit consists of only three load cells forming three vertices of a triangular pattern, to collect at least one information regarding a posture of the user, ballistocardiograph and body weight of the user,
   wherein a transmission unit connected to the pressure detection unit comprises an interface module comprising a microprocessor receiving the collection of information and transmitting the collected information to a terminal; and
   a non-transitory physical storage medium storing program code and connected to the microprocessor, the program code, when executed by the microprocessor, causes the microprocessor to:
   collect data comprising a population of users of the chair, a period of time the users in the population sitting on the chair, posture change frequency of the users during the time period, and age profile of each individual in the population;
   calculate a vector difference between the user's initial center of gravity in the chair based on distributed loads applied to the three load cells and the user's center of gravity recalculated in the chair based on changing distributed loads acting on the three load cells responding to the user's posture change in the chair, wherein the initial and recalculated centers of gravity are placed in the triangular pattern;

define a standard posture change frequency of an age group in the population by calculating an average frequency of posture change of the age group;

generate a set of scores responding to the posture change frequency of individuals in the age group;

measure posture change frequency of an individual sitting on the chair;

generate a score in the set of scores responding to the measured posture change frequency; and generate a parameter to determine a degree of the distraction of the individual by correlating the generated score and a brain state of the individual provided through the transmission unit.

2. The system according to 1, wherein the pressure detection unit further comprises an upper disk having a upper disk outer edge and a lower disk having lower disk outer edge so that the three load cells are placed between the upper disk and the lower disk and each of the three load cells are placed near the upper disk outer edge and the lower disk outer edge.

3. The system according to 2, wherein the transmission unit is placed between the seating unit and the pressure detection unit.

4. The system according to 3, wherein the transmission unit further comprises an analog circuit configured to receive the collection of information and transmit the collected information to the interface module.

5. The system according to 3, wherein the microprocessor is configured to convert analog signals of the collection of information to digital signals to be transmitted to the terminal.

6. The system according to 5, wherein the microprocessor is configured to:

monitor a posture change or type of motion in the form of frequency and intensity, estimate the posture information by separating frequency information of the posture change and intensity information of the posture change, and reflect the posture information on the evaluation of degree of distraction.

7. The system according to of claim 6, wherein microprocessor is configured to receive and process the frequency information of the posture change which include the number of generations per unit time of an inducing factor of the posture change responding to the user's motion and the intensity information of the posture change is directionality as a magnitude of the motion.

8. The system according to claim 7, wherein the microprocessor is further configured to provide a posture change rate indicator comprising the frequency of the posture change and the intensity of the posture change, both extracted upon the monitoring of the posture change, and wherein the microprocessor is further configured to calculates an average frequency through a measurement experiment and a statistical analysis in real time, and wherein the microprocessor is further configured to provide the frequency by scoring the frequency based on a standard deviation using an intermediate value as an average value.

9. The system of claim 8, wherein the microprocessor is further configured to receive a brain wave signal from an external brain wave measuring device connected to the interface module in order to generate a degree-of-distraction index through the analysis and comparison of brain waves, and the microprocess is further configured to conduct comparison and evaluation based on preset reference brain wave information to determine whether the brain wave information measured in the left brain in a state where concentration is low, brain wave information measured in the left brain in a state where concentration is high, brain wave information measured in the right brain in a state where concentration is low, and brain wave information measured in the right brain in a state where concentration is high, and wherein the brain wave measuring device is configured to analyze an alpha ($\alpha$) wave and an SMR wave of a brain wave to determine whether the posture information is in a seated state and the brain wave measuring device is also configured to simultaneously measure the brain wave with the posture information upon the monitoring of the brain wave signal at a concentrated state and an unconcentrated state, and the brain wave measuring device is configured to analyze the correlation between the extracted brain wave and the degree of distraction to generate a degree-of-distraction parameter.

10. The system according to claim 6, wherein the microprocessor is further configured to:

generate a standard posture of the user by calculating the user weights applied to the three load cells when the user first sits in the chair, and measure a changing posture of the user shifted from the reference sitting posture based on measurements of the weights applied to the three sensors, wherein the changing posture is identified by the numbers of weight shift between the three load cells over a period of time specified and a degree of the weight shift.

11. A system for estimating a degree of distraction of a user based on unconstrained bio-information obtained from the user, comprising:

a chair comprising a seating unit, a pressure detection unit and a support unit, wherein the pressure detection unit is located between the seating unit and the support unit, wherein the pressure detection unit comprising a smart sensor detecting a change in body weight distribution of the user, consisting of only three load cells forming three vertices of a triangular pattern, wherein the three load cells are configured to gather a collection of information comprising at least one or more of information on posture of the user, information for ballistocardiograph and information on the user's body weight, wherein a transmission unit connected to the pressure detection unit comprises of an interface module comprising a microprocessor receiving the collection of information and transmitting the collected information to a terminal; and a non-transitory physical storage medium storing program code and connected to the microprocessor, the program code, when executed by the microprocessor, causes the microprocessor to:

collect data comprising a population of users of the chair, a period of time the users in the population sitting on the chair, posture change frequency of the users during the time period, and age profile of each individual in the population;

calculate a vector difference between the user's initial center of gravity in the chair based on distributed loads applied to the three load cells and the user's center of gravity recalculated in the chair based on changing distributed loads acting on the three load cells responding to the user's posture change in the chair, wherein the initial and recalculated centers of gravity are placed in the triangular pattern;

define a standard posture change frequency of an age group in the population by calculating an average frequency of posture change of the age group;

generate a set of scores responding to the posture change frequency of individuals in the age group;

measure posture change frequency of an individual sitting on the chair;

generate a score in the set of scores responding to the measured posture change frequency; and generate a parameter to determine a degree of the distraction of the individual by correlating the generated score and a brain state of the individual provided through the transmission unit.

12. The system according to 11, wherein the pressure detection unit further comprises an upper disk having a upper disk outer edge and a lower disk having lower disk outer edge so that the three load cells are placed between the upper disk and the lower disk and each of the three load cells are placed near the upper disk outer edge and the lower disk outer edge.

13. The system according to 12, wherein the transmission unit is placed between the seating unit and the pressure detection unit.

14. The system according to 13, wherein the transmission unit further comprises an analog circuit configured to receive the collection of information and transmit the collected information to the interface module.

15. The system according to 14, wherein the microprocessor is configured to convert analog signals of the collection of information to digital signals to be transmitted to the terminal.

16. The system according to 15, wherein the microprocessor is configured to:
monitor a posture change or type of motion in the form of frequency and intensity,
estimate the posture information by separating frequency information of the posture change and intensity information of the posture change, and
reflect the posture information on the evaluation of degree of distraction.

17. The system according to of claim 16, wherein microprocessor is configured to receive and process the frequency information of the posture change representing the number of generations per unit time of an inducing factor of the posture change corresponding to the user's motion and the intensity information of the posture change represents directionality as a magnitude of the user's motion.

18. The system according to claim 17, wherein the microprocessor is further configured to provide a posture change rate indicator comprising the frequency of the posture change and the intensity of the posture change, both extracted upon the monitoring of the posture change, and wherein the microprocessor is further configured to calculates an average frequency through a measurement experiment and a statistical analysis in real time, and wherein the microprocessor is further configured to provide the frequency by scoring the frequency based on a standard deviation using an intermediate value as an average value.

19. The system of claim 18, wherein the microprocessor is further configured to receive a brain wave signal from an external brain wave measuring device connected to the interface module in order to generate a degree-of-distraction index through the analysis and comparison of brain waves, and the microprocessor is further configured to conduct comparison and evaluation based on preset reference brain wave information to determine whether the brain wave information measured in the left brain in a state where concentration is low, brain wave information measured in the left brain in a state where concentration is high, brain wave information measured in the right brain in a state where concentration is low, and brain wave information measured in the right brain in a state where concentration is high, and
wherein the brain wave measuring device is configured to analyze an alpha ($\alpha$) wave and an SMR wave of a brain wave to determine whether the posture information is in a seated state and the brain wave measuring device is also configured to simultaneously measure the brain wave with the posture information upon the monitoring of the brain wave signal at a concentrated state and an unconcentrated state, and the brain wave measuring device is configured to analyze the correlation between the extracted brain wave and the degree of distraction to generate a degree-of-distraction parameter.

20. The system according to claim 15, wherein the microprocessor is further configured to:
generate a standard posture of the user by calculating the user weights applied to the three load cells when the user first sits in the chair, and
measure a changing posture of the user shifted from the reference sitting posture based on measurements of the weights applied to the three sensors, wherein the changing posture is identified by the numbers of weight shift between the three load cells over a period of time specified and a degree of the weight shift.

* * * * *